United States Patent

Samuelsen et al.

[11] Patent Number: 6,153,215
[45] Date of Patent: Nov. 28, 2000

[54] DRESSING FOR DOSING ONE OR MORE MEDICAMENTS

[75] Inventors: Peter Boman Samuelsen, Rungsted Kyst; Dorte Ulrik Nielsen, Virum, both of Denmark

[73] Assignee: Colorplast A/S, Denmark

[21] Appl. No.: 08/387,935

[22] PCT Filed: Aug. 26, 1993

[86] PCT No.: PCT/DK93/00278

§ 371 Date: Feb. 27, 1995

§ 102(e) Date: Feb. 27, 1995

[87] PCT Pub. No.: WO94/05340

PCT Pub. Date: Mar. 17, 1994

[30] Foreign Application Priority Data

Aug. 27, 1992 [DK] Denmark .................. 1061/92

[51] Int. Cl.[7] .................................................. A61L 15/44
[52] U.S. Cl. ........................................... 424/448; 424/449
[58] Field of Search ............................. 429/448, 449

[56] References Cited

U.S. PATENT DOCUMENTS

| | | | |
|---|---|---|---|
| 4,904,247 | 2/1990 | Therriault et al. ............... | 604/304 |
| 5,066,494 | 11/1991 | Becher .......................... | 424/448 |
| 5,132,115 | 7/1992 | Wolter .......................... | 424/448 |
| 5,149,538 | 9/1992 | Granger ......................... | 424/449 |
| 5,176,915 | 1/1993 | Hoffmann ........................ | 424/445 |
| 5,230,898 | 7/1993 | Horstmann ....................... | 424/449 |

FOREIGN PATENT DOCUMENTS

| | | |
|---|---|---|
| 0272149 | 6/1988 | European Pat. Off. . |
| 0307187 | 3/1989 | European Pat. Off. . |

*Primary Examiner*—Thurman K. Page
*Assistant Examiner*—Isis A. D. Ghali
*Attorney, Agent, or Firm*—Ostrolenk, Faber, Gerb & Soffen, LLP

[57] ABSTRACT

A dressing for dosing one or more medicaments comprising at least one medicament containing layer (2, 2a, 2b) and a barrier layer (1, 1a, 1b) arranged between the medicament containing layer and the release face (6, 6a), said barrier layer consisting of a continuous hydrophobic phase and a discontinuous hydrophilic phase which is dispersed therein and which is water soluble or water swellable. Desired medicament release rates and release profiles within very wide limits may be obtained with the dressing.

21 Claims, 1 Drawing Sheet

DRESSING FOR DOSING ONE OR MORE MEDICAMENTS

This application is a 371 of PCT/DK93/00278 filed Aug. 26, 1993.

BACKGROUND OF THE INVENTION

The present invention concerns a dressing containing one or more active medicaments for controlled release.

Various bandages or dressings of this type are known, consisting of (a) A non-adhesive water-tight film, foam or the like arranged on the side of the bandage which is not intended to face the patient's skin.

(b) A layer of an adhesive material consisting of a continuous phase containing an adhesive and e.g. composed of an elastomer, a plasticizer for elastomers, a tackifying resin and optionally an oil-based extender as well as an antioxidant, and optionally one or more water soluble or water swellable hydrocolloids, such as starch or cellulose derivatives or other hydrophilic polymers, as well as medicaments, such as antiseptics, antibiotics and antiinflammatory agents.

(c) A removable release layer.

Such bandages, which are primarily intended for use on wounded skin areas, are known e.g. from EP Patent Applications Nos. 92999 and 122344 as well as from DK Patent No. 154 806.

Other bandages of a similar type, but which are also used for transcutaneous medication, are known from U.S. Pat. No. 4,904,247 and from EP Patent Application No. 186019.

With the exception of the bandage known from DK Patent No. 154 806, it is not possible to control or regulate the release of medicament from the bandages mentioned above.

Thus, in the use of these known bandages the initial release will be very great, following which the release of the medicaments decreases evenly.

The adhesive layer of the bandage described in DK Patent No. 154 806 consists of a continuous water insoluble phase and a discontinuous phase which is dispersed in it and which is water soluble or water swellable, said discontinuous phase incorporating the medicament. Thus, the incorporated medicament will be released in step with the solution or swelling of liquid in the discontinuous phase, and there is thus no control of the release of the medicament.

However, a great initial release and a following declining release of the medicament can still be observed when the bandage is used on exuding wounds, and in particular if the wounds are very exuding.

Such a release profile is desired in some situations, but in other situations another release profile is desired, such as release of a constant amount of the medicament per unit of time or delayed release.

Furthermore, U.S. Pat. No. 4,904,247 describes a liquid absorbing wound bandage comprising an adhesive absorbing layer intended to face the user as well as a non-adhesive layer, wherein one of the layers or both may contain a medicament for transdermal release.

The two layers are hydrogels consisting of mixtures of hydrophilic and hydrophobic polymers, the mixture in the adhesive layer comprising at least 80% hydrophilic polymer forming a continuous matrix in which the hydrophobic polymer is dispersed.

The release of medicaments takes place by dispersion through the hydrophilic moist matrix. Thus, theoretically it is possible to obtain delayed release of the medicament by selecting an adhesive hydrogel layer without medicament. However, in practice the medicament spreads in the layers during storage, thus resulting in a release profile of the medicament which corresponds to the one obtained with the bandages mentioned above.

U.S. Pat. No. 4,781,924 discloses a bandage for release of one or more medicaments at a predetermined rate, said bandage consisting of several layers, wherein the active compound is incorporated in a first form in which it cannot be released and is changed to another form by an activating compound, which is additionally activated by water. Thus, the release from this bandage is likewise regulated by liquid action, and the release profile is substantially analogous with the release profile of the bandage known from DK Patent No. 154 806, it being possible, however, to obtain delayed release of the medicament. Thus, this bandage can only be used for quite few medicament systems and is moreover rather expensive to manufacture.

NO Published Application No. 163 438 discloses a plaster comprising a medicament reservoir which is coated with a semipermeable or perforated film membrane on the central part of the side facing the skin and is coated with an adhesive layer on the peripheral part of this side, and also the membrane may optionally be coated with adhesive. Delayed release is likewise possible with a such a plaster. However, the plaster has a very complicated structure and is thus very expensive to manufacture.

EP Patent Specification No. 144 486 discloses a bandage for transcutaneous medication and consisting of an impermeable backing layer, the reservoir layers having a medicament concentration which is above the saturation point; the medicament concentration of the layer increases from the reservoir layer facing the adhesive layer to the reservoir layer facing the backing layer.

None of these layers is mentioned as a membrane or a release controlling layer, nor is it mentioned how such a membrane effect or release controlling effect can be adjusted. If such a bandage is used directly after the manufacture, it is thus very likely, as also shown in the examples, that an increasing release of the medicament will occur and possibly also a delayed release. However, it is not mentioned how the medicament concentration differences are kept stable in the individual reservoir layers and in the adhesive layer during storage. Since the vehicle in the exemplified bandages is the same in the various layers and other components having a membrane function are not incorporated, the medicament concentration differences will be balanced completely or partly during storage, which means that the actual release profile is unpredictable when using a stored product.

Thus, such a bandage cannot be constructed to have a predetermined release profile.

EP Patent Application No. 249 343 discloses a bandage comprising a medicament reservoir and a delay layer which is interposed between the reservoir and the skin and which is impermeable to the medicament in a dry state and permeable to the medicament in a hydrated state. With this bandage it is possible to delay the initial release of the medicament. Once the release has begun, it is not possible, however, to control the rate of it.

Another type of membrane controlled transcutaneous medication bandage is mentioned in Application WO89/12470. This bandage comprises a medicament reservoir of liquid medicament, a membrane layer of an LDPE or EVE film as well as an adhesive layer which is very permeable to the medicament. With this bandage it is possible to obtain a reasonably constant release rate over a long period, but there will still be a very high initial release from the bandage. With the bandage it is not possible, however, to design other release profiles, and the bandage can moreover only be used for transcutaneous dosing of a limited number of medicaments.

EP Patent Specification 259 136 discloses a transcutaneous medication bandage comprising a layer of ethylene/vinyl acetate polymer containing the medicament in a high concentration and an adhesive layer of mineral oil/polyisobuthylene. The diffusion coefficient of the given medicament is considerably higher in the ethylene/vinyl acetate polymer layer than in the mineral oil/polyisobuthylene layer. This means that the mineral oil/polyisobuthylene layer essentially determines the release rate, and it is thus possible to obtain a bandage which has a constant release rate over a long period. However, it does not appear how this release rate can be profiled.

Thus, a large number of different mineral medication bandages are known, useful for dosing various medicaments with a delayed or constant release profile. However, most of these bandages can only be used for few medicament types. Furthermore, these bandages are very restricted with respect to the release profiles and release rates that can be obtained, and it is simultaneously a rather complicated process, which often requires many tests, to adjust or change release profiles and rates within the possible range.

The object of the present invention is to provide a dressing containing one or more medicaments and having a composition which makes it possible to design release profiles and rates within a very wide range.

SUMMARY OF THE INVENTION

A dressing for dosing one or more medicaments and comprises at least one medicament containing layer and a barrier layer arranged between the medicament containing layer and a release face characterized in that the barrier layer has a continuous hydrophobic phase and a discontinuous hydrophilic phase which is dispersed therein and which is water swellable.

DESCRIPTION OF THE INVENTION

In the construction of a dressing according to the invention with one or more selected medicaments, the degrees of freedom are numerous, which, generally speaking, makes it possible to obtain desired release profiles and rates.

Thus, with the dressing of the invention it is possible to obtain a large number of different release profiles and rates of one or more medicaments, and dressings having desired release profiles and rates can moreover be reproduced with great certainty.

Further, the dressing of the invention can be used for dosing a large number of different hydrophilic as well as hydrophobic medicaments and combinations of these.

For example, the dressing of the invention having one release profile enables several maxima and minima to be obtained, or if the dressing contain both hydrophilic and hydrophobic medicaments, the release profile of these medicaments can essentially be independent of each other.

The dressing of the invention can be used for both transcutaneous medication (TDD medication) and for medication in exuding wounded areas.

In the construction of the dressing of the invention it is thus to be considered whether the medicament or medicaments are to be released by liquid activation or non-liquid activation (i.e. no activation) or a combination of the liquid activation and non-liquid activation.

A medicament to be released by liquid activation is incorporated in the discontinuous phase of a reservoir layer consisting of a continuous hydrophobic phase and discontinuous hydrophilic phase. The hydrophobic phase is composed of a cross-linked polymer optionally containing an adhesive, said hydrophobic phase being preferably composed of an elastomer, a plasticizer for elastomers, a tackifying resin and optionally an oil-based extender as well as an antioxidant, a continuous phase containing (a) a physically cross-linked elastomer in the form of polyisobutylene, one or more styrene olefin styrene block copolymers or ethylene propylene block copolymers, and optionally containing one or more of components b–e (b) a hydrocarbon resin in the form of a polymer or copolymer of cyclopentadiene, dicyclopentadiene, α-pinene and/or β-pinene, (c) an antioxidant, (d) an oil extender consisting of one or more mineral oils, and (e) an elastomer polar plasticizer, such as e.g. an ester of an polyethylene glycol or polypropylene glycol, or an ester of a di- or polybasic carboxylic acid with a preferably aliphatic alcohol, being particularly preferred.

The hydrophobic phase has dispersed in it a discontinuous hydrophilic phase, which is water soluble or water swellable and preferably consists of one or more water soluble or water swellable hydrocolloids, starch or cellulose derivatives or hydrophilic polymers.

A dressing according to the invention may have two or more different medicaments incorporated for release by liquid activation. Such different medicaments may e.g. be incorporated in the discontinuous phase in the same reservoir layer, or the different medicaments may be incorporated in the discontinuous phase in their respective reservoir layers.

When several medicaments are incorporated for release by liquid activation in the same dressing, care must be taken that the medicaments do not inexpediently react chemically with each other.

A medicament to be released by non-liquid activiation is incorporated in a continuous hydrophobic reservoir layer, optionally in a liquid state, as is known from NO Published Application No. 163 438, or in a liquid state incorporated in capsules which are broken by pressure or rubbing. However, a hydrophobic cross-linked polymer of the same type as stated above is preferred as a reservoir layer. A discontinuous hydrophilic phase of the same type as stated above may optionally be dispersed in the continuous hydrophobic phase.

All things considered, the reservoir layer or layers preferably have a filling degree of 0–60% by volume. By filling degree is meant the relative or percentage amount of hydrophilic phase.

If the medicament is incorporated in the hydrophilic phase in the reservoir layer, the layer preferably has a filling degree of 10–60% by volume and in particular 30–50% by volume.

If the medicament is incorporated in the hydrophobic phase in the reservoir layer, the layer preferably has a filling degree of 0–50% by volume and in particular 10–30% by volume, but the filling degree is not greater than the filling degree in the barrier layer.

If a medicament is incorporated in both the hydrophilic phase and the hydrophobic phase in the reservoir layer, the layer preferably has a filling degree of 10–50% by volume and in particular 20–40% by volume, but the filling degree is not greater than in the barrier layer.

Thus, the two release principles may be combined in the same dressing, e.g. by incorporating two different medicaments in the same reservoir layer, one medicament being incorporated in the continuous phase, the other in the discontinuous phase, or by the dressing having two reservoir layers in a first reservoir layer with incorporated medicament in the discontinuous phase and a second reservoir layer with a medicament incorporated in a continuous phase.

The hydrophobic phase of the barrier layer consists of a hydrophobic cross-linked polymer, preferably of a composition as stated before, and the discontinuous phase likewise preferably has the previously stated composition. A barrier layer having this preferred composition is thus adhesive, and if the barrier layer constitutes the face facing toward the skin in use, the dressing is adhesive. However, the face facing toward the skin in use may also be non-adhesive, the dressing being in that case retained against the skin by a secondary bandage. Additionally, the dressing of the invention may have a layer of an adhesive without a barrier effect, said layer being permeable to the medicament and constituting the face facing toward the skin in use. Such an adhesive layer may advantageously be discontinuous, i.e. applied in a pattern so that not all the membrane face is covered.

If the dressing is to be used without a secondary bandage, the face facing away from the skin in use is to be coated with a non-adhesive water-tight film layer of e.g. polyurethane or a non-adhesive water-tight layer of foam or the like. This top layer is preferably permeable to water vapour. Further, the film layer or the foam layer must be selected such that it essentially prevents loss of medicament by diffusion through the layer.

The barrier layer may additionally contain one or more medicaments which are incorporated in the same manner as described in the discussion of the reservoir layer, but the amount of the medicament in the barrier layer is preferably smaller than the amount in the reservoir layer. If the medicament is hydrophobic and incorporated in a hydrophobic phase in the reservoir layer, medicament will diffuse into the barrier layer during storage. This amount is substantially constant for a given structure of a bandage.

The dressing may have several barrier layers of uniform or disuniform filling degree, a first barrier layer being arranged between the release face and a first reservoir layer, the other barrier layer or layers being arranged between reservoir layers content of medicament in the same or different.

Additionally, a liquid absorbing medicament-free layer, preferably of the same structure as the barrier layer and in particular with a filling degree of more than 40% by volume, may be arranged between the reservoir layer or, if several such layers are provided, between the upper (most remote from the skin in use) reservoir layer and the upper face.

The dressing is particularly useful for dosing medicaments, such as antiseptics/antibiotics (e.g. chlorohexidine, povidone iodine, silver nitrate, silver sulphadiazine, fucidine), substances for cleaning chronic wounds (e.g. proteolytic enzymes), substances controlling growth in the wound (e.g. cytokins such as epidermal growth factor, fibroplast growth factor, interleucins, growth hormone, etc.) or other factors (e.g. minerals such as Ca, Zn, Mg, Cu, and the like, vitamins and the like).

These medicaments are preferably incorporated in the discontinuous phase, e.g. by the method described in DK Patent Specification No. 154806.

The dressing of the invention is moreover particularly useful for dosing medicaments such as hormones (e.g. estradiol), antiinflammatory agents (e.g. D vitamin analogs), analgesics (e.g. lidocain), antirheumatic agents, nicotinamide, etc.

These medicaments are preferably incorporated in the continuous phase e.g. by simple mixing. If the medicaments per se are not completely or partly lipophilic, they may be coupled to or be incapsulated with lipophilic compounds.

The structure and the dimension of the dressing of the invention depends greatly upon the medicament or medicaments to be dosed.

As regards the dimension, however, dressings having an area of between 1–200 $cm^2$, in particularly 2–10 $cm^2$ and a thickness of between 100–800 $\mu$m are preferred.

The barrier layer or each of the barrier layers preferably has a thickness of between 25 and 75 $\mu$m and a filling degree of 20–60% by volume.

If the medicament is incorporated in the continuous phase, an increased filling degree in the membrane layer results in a reduced medicament release rate, and if the medicament is incorporated in the discontinuous phase, an increased filling degree in the membrane layer results in an increased medicament release rate.

The dressing preferably has 1–3 medicament reservoirs having the same or a different content of medicament. Each of these reservoir layers preferably has a thickness of 50–250 $\mu$m.

The dressing may moreover contain one or more enhancers (compounds increasing the transport of medicament) in the reservoir layers and/or the barrier layers. Examples of enhancers include dioctyl adiapate, DMSO, low mole PEG and other glycols.

The invention will be described more fully below and with reference to the drawings and the examples.

DETAILED DESCRIPTION OF THE DRAWINGS

The shown dressings are not exact exemplifications, but just serve to illustrate particularly good structures of the dressing of the invention.

Figure 1:
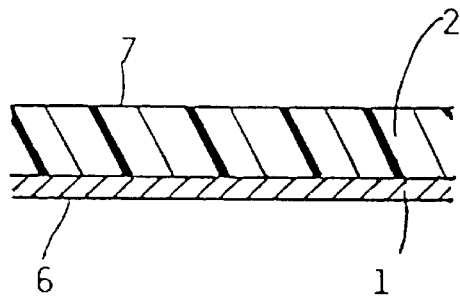
FIG. 1 is a cross-section of a first embodiment of a dressing according to the invention.

The dressing shown in FIG. 1 consists of a barrier layer 1, which has the composition stated previously and also optionally contains one or more medicaments in the hydrophobic phase and/or in the hydrophilic phase. A reservoir layer 2 containing one or more medicaments, as stated before, is provided on one side of the layer 1. The other side of the layer 1 is adhesive or non-adhesive and is intended to be placed against the user's skin or wounds, following which the dressing is fixed by means of a secondary bandage which is essentially impermeable to the medicament or medicaments in the dressing. When sold, the two free faces 6 and 7 of the dressing are coated with removable cover layers which are removed prior to use. These cover layers may optionally be formed by the package.

Figure 2:
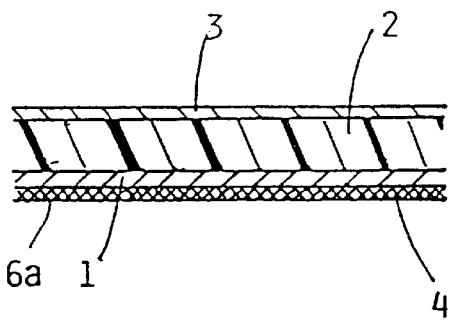
FIG. 2 is a cross-section of a second embodiment of a dressing according to the invention.

The dressing shown in FIG. 2 has a reservoir layer 2 and a barrier layer 1 corresponding to the layers 1 and 2 shown in FIG. 1. The face of the barrier layer 1 facing away from the reservoir layer 2 is additionally coated with an adhesive layer 4 which has no substantial barrier effect. This adhesive layer may e.g. be applied in a pattern so as to cover 25–75% of the surface of the barrier layer. The face of the reservoir layer 2 facing away from the barrier layer 1 is coated with a liquid impermeable and substantially medicament impermeable non-adhesiver layer 3 in the form e.g. a polymer film, foam or the like. This dressing may be used without a secondary bandage. When the product is sold, the adhesive face 6a is coated with a removable cover layer.

Figure 3:
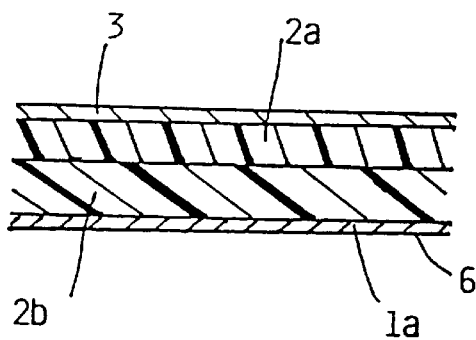
FIG. 3 is a cross-section of a third embodiment of a dressing according to the invention.

The dressing shown in FIG. 3 has a barrier layer 1a corresponding to the barrier layer 1 in FIG. 1, but the barrier layer 1a has an adhesive face 6 which, when sold, is coated with a removable cover layer. The dressing likewise has a non-adhesive layer 3 corresponding to the non-adhesive layer 3 in FIG. 2. Two reservoir layers 2a and 2b having the same or a different thickness are interposed between the two layers 1 and 3. The two reservoir layers independently contain one or more medicaments in amounts which are likewise independent of each other. If the two reservoir layers are composed of a continuous hydrophobic phase and a discontinuous hydrophilic phase, as described before, it is particularly preferred that the hydrophobic phase has the same composition in both layers. In the same manner, the dressing of the invention may have three or more reservoir layers.

Figure 4:
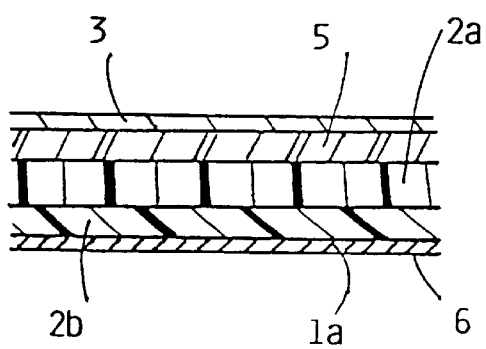
FIG. 4 is a cross-section of a fourth embodiment of a dressing according to the invention.

The dressing shown in FIG. 4 has a barrier layer 1a with an adhesive face 6, two reservoir layers 2a and 2b as well as a non-adhesive layer 3 corresponding to the parts shown with the same reference numerals in FIG. 3. A medicament release promoting layer 5 is interposed between the reservoir 2a and the non-adhesive layer 3. The release promoting layer 5 contains a liquid absorbing component and may advantageously be built in the same manner as the barrier layer, i.e. with a continuous phase and a discontinuous phase, containing hydrocolloid, dispersed therein. Such a release promoting layer preferably has a filling degree of 10–60% by volume and in particularly of 40–60% by volume.

Figure 5:
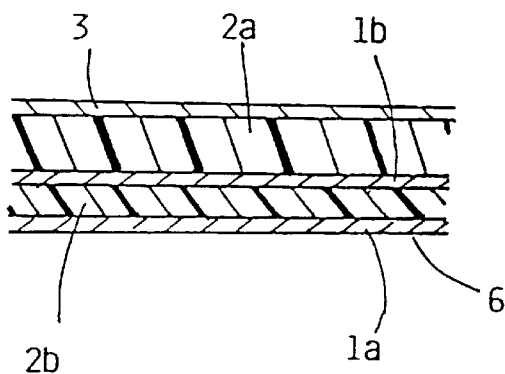
FIG. 5 is a cross-section of a fifth embodiment of a dressing according to the invention.

The dressing shown in FIG. 5 has two reservoir layers 2a and 2b as well as a non-adhesive layer, which correspond to the layers with the same reference numerals described before. The dressing additionally has a first barrier layer 1a, which corresponds to the previously described barrier layers 1a, and which has an adhesive face. Further, a second barrier layer 1b, which has the same composition as the previously described barrier layer 1, is interposed between the two reservoir layers 2a and 2b. The barrier layers 1a and 1b may have the same or different composition, including the same or different filling degree.

The following components are used in the examples:

| Trade names | |
|---|---|
| Styrene isoprene block copolymer | Cariflex TR ®, (Shell) |
| Synthetic resin | Regalite ®, (Hercules) |
| Growth hormone (hGH) | Norditropin ®, (Novo Nordisk) |
| Trypsin | Trypure ®, (Novo Nordisk) |
| Gelatine | (USP) |
| Paraffin oil | (USP) |
| Hydroxyethylcellulose (HEC) | Natrosol ®, (Hercules) |
| NaCMC | Blanose ®, (Hercules) |
| Triamcinolone acetomide | (Ammersham) |
| Insulin | Actraphan ®, (Novo Nordisk A/S) |
| Polyurethane film | Estane ®, (Goodrich) |

EXAMPLE 1

A dressing consisting of three layers was manufactured.

The three layers had a continuous phase and a discontinuous phase, all with a filling degree of 50% by weight.

The continuous phase was reduced by dissolving styrene isoprene block copolymer, synthetic resin and dioctyl adipate in toluene in the ratio 2:3.

The trypsin gelatine complex was produced in the weight ratio 1:9 by freeze drying from an aquous buffer solution. Following freeze drying, the complex was ground to a particle size of less than 100 μm.

The discontinuous phase was produced by dissolving sodium carboxymethylcellulose (NaCMC) in $H_2O$ to a concentration of about 2% by weight. Then gelatine and/or trypsin gelatine complex was added, and the mixture was freeze dried and ground to a particle size of less than 100 μm.

Three portion of discontinuous phase were admixed with their respective continuous phases, following which the first layer a was applied by a film applicator on silicone coated paper. After evaporation of toluene, the second layer b was applied on the a layer, and the third layer c was applied in the same manner on the b layer.

Table 1 shows the composition and thickness of the three layers.

TABLE 1

| | | a | b | c |
|---|---|---|---|---|
| Continuous phase | Styrene isoprene block copolymer (Weight %) | 12.5 | 12.5 | 12.5 |
| | Resin (weight %) | 25 | 25 | 25 |
| | Paraffin oil (weight %) | 12.5 | 12.5 | 12.5 |
| Discontinuous phase | NaCMC (weight %) | 45 | 45 | 45 |
| | Trypsin gelatine complex (weight %) | 5 | 0 | 0.5 |
| | Gelatine (weight %) | 0 | 5 | 4.5 |
| | Thickness (μm) | 50 | 200 | 50 |

The product was placed in the bottom of a chamber with the a layer sticking to the bottom, so that the release of the medicament took place through the c layer. The release medium was a 20 mM Tris buffer. The test was performed at 37° C., and samples were taken after 2, 4, 6, 8, 24, 48 and 72 hours.

For comparison, a dressing consisting of the c layer alone was tested in the same manner.

Released trypsin (μg) is stated in table 2.

TABLE 2

| h | 2 | 4 | 6 | 8 | 24 | 48 | 72 |
|---|---|---|---|---|---|---|---|
| product of inv. | 1.7 | 3.1 | 3.1 | 12.7 | 18.6 | 31.0 | 31.0 |
| C layer alone | 1.7 | 3.0 | 3.0 | 3.2 | 3.4 | 3.5 | 3.5 |

For the C layer alone, it will be seen that substantially no more trypsin is released after 4 hours. For the product of the invention, it will be seen that the first dose was released within the first 4 hours, and then no trypsin was released for a period of about 2 hours, following which a new and longer dosing period began.

EXAMPLE 2

A dressing consisting of three layers having a uniform thickness and varying filling degree was manufactured.

The product was manufactured in the same manner as in example 1, using HEC instead of NaCMC, and using as the medicament growth hormone (hGH) in the form of a hGH gelatine complex produced in the weight ratio 1:9 by freeze drying from an aqueous buffer solution and ground to a particle size of less than 100 μm.

Table 3 shows the composition and thickness of the layers.

TABLE 3

| | | a | b | c |
|---|---|---|---|---|
| Continuous phase | Styrene isoprene copolymer (weight %) | 12.5 | 20 | 12.5 |
| | Resin (weight %) | 25 | 40 | 25 |
| | Paraffin oil (weight %) | 12.5 | 20 | 12.5 |
| Discontinuous phase | HEC (weight %) | 45 | 20 | 1 |
| | hGH gelatine (weight %) | 5 | 0 | 1 |
| | Gelatine (weight %) | 0 | 0 | 4 |
| | Thickness (μm) | 50 | 50 | 50 |

The product was placed in the bottom of a chamber with the a layer sticking to the bottom. The release medium was a 20 mM Tris buffer with 0.1% albumin. The test was performed at 37° C., and samples were taken after 2, 4, 6, 8, 24, 48 and 72 hours.

Released hGH (μg) is stated in table 4.

TABLE 4

| h | 2 | 4 | 6 | 8 | 24 | 48 | 72 |
|---|---|---|---|---|---|---|---|
| | 1.7 | 3.1 | 3.1 | 3.2 | 12.7 | 21.0 | 21.2 |

As was the case in example 1, hGH was released in two intervals.

EXAMPLE 3

Three dressings I, II and III, each consisting of two layers, were manufactured.

The layers were manufactured and laminated in the same manner as described in example 2.

The a layer had the same composition and thickness in all the products.

The composition and thickness of the layers are stated in table 5.

TABLE 5

| | | a | bI | bII | bIII |
|---|---|---|---|---|---|
| Continuous phase | Styrene isoprene block copolymer (weight %) | 24 | 36 | 32 | 24 |
| | Resin (weight %) | 30 | 45 | 40 | 30 |
| | Dioctyl adipate (weight %) | 6 | 9 | 8 | 6 |
| Discontinuous phase | HEC (weight %) | 35 | 10 | 20 | 40 |
| | hGH gelatine (weight %) | 5 | 0 | 0 | 0 |
| | Gelatine (weight %) | 0 | 0 | 0 | 0 |
| | Thickness (μm) | 50 | 100 | 100 | 100 |

The dressings were tested as described in example 2, and samples were taken after 4, 6, 8, 24 and 48 hours. A dressing consisting of the a layer alone was tested at the same time.

Released hGH in % of the incorporated amount of hGH is stated in table 6.

TABLE 6

| Product h | 4 | 6 | 8 | 24 | 48 |
|---|---|---|---|---|---|
| Pure a layer | 12 | 25 | 55 | 55 | 55 |
| I | 3 | 5.5 | 35 | 49 | 55 |
| II | 3 | 7.5 | 52 | 53 | 53 |
| III | 10 | 15 | 53 | 55 | 55 |

It will be seen that the lower the filling degree in the b layer, the greater the delay in hGH release from the a layer, low HEC concentration giving slow swelling of the b layer.

EXAMPLE 4

Three two-layered dressings having a varying thickness of the b layer were manufactured as described in the previous examples, the used medicament being insulin in the form of an insulin gelatine complex produced in the weight ratio 1:9 in the same manner as the previous medicament complexes.

The composition of the a layer and the b layer, respectively, was the same for all products.

The composition and thickness of the layers in the three products are stated in table 7.

TABLE 7

| | | a | b |
|---|---|---|---|
| Continuous phase | Styrene isoprene block copolymer (weight %) | 22 | 22 |
| | Resin (weight %) | 27.5 | 27.5 |
| | Dioctyl adipate (weight %) | 5.5 | 5.5 |
| Discontinuous phase | NaCMC (weight %) | 40 | 45 |
| | Trypsin gelatine complex (weight %) | 5 | 0 |
| | Gelatine (weight %) | 0 | 5 |
| | Product I Thickness (μm) | 50 | 50 |
| | Product II Thickness (μm) | 50 | 200 |
| | Product III Thickness (μm) | 50 | 400 |

The three dressings as well as a product consisting of the a layer in a thickness of 50 μm were tested like in example 2.

Released insulin in % of incorporated insulin is stated in table 8.

TABLE 8

| Product h | 4 | 6 | 8 | 24 | 48 | 72 |
|---|---|---|---|---|---|---|
| a layer | 40 | 45 | 50 | 60 | 60 | 60 |
| I | 25 | 32 | 37 | 55 | 55 | 55 |
| II | 2 | 6 | 10 | 35 | 50 | 55 |
| III | 1 | 2 | 5 | 20 | 30 | 45 |

The results show that increasing thickness of the b layer delays the release of insulin, the diffusion zone through the b layer being increased.

EXAMPLE 5

Two dressings I and II of three layers each were manufactured, one of the three layers (the a layer) being a polyurethane layer. The two other layers consisted of a continuous phase and a discontinuous phase.

The discontinuous phase consisted of NaCMC (2601 ENKA) in both layers.

The continuous phase consisted of styrene isoprene block copolymer, resin and paraffin oil and was produced as stated in the previous examples. Further, tritium labelled triamcinolone acetonide was added in one layer (the b layer).

This b layer was likewise the same for the two products.

The composition and the thickness of the two dressings are stated in table 9. The values are part by volume, unless otherwise stated.

TABLE 9

|  | a | b | CI | CII |
|---|---|---|---|---|
| Styrene isoprene block copolymer | — | 20 | 20 | 20 |
| Resin | — | 40 | 40 | 40 |
| Paraffin oil | — | 40 | 40 | 40 |
| NaCMC | — | — | 10 | 50 |
| Triamcinolone acetoid (g/100 g continuous phase) | — | 0.36 | — | — |
| Polyurethane | 100% | — | — | — |
| Product I thickness ($\mu$m) | 30 | 250 | 50 | — |
| Product II thickness ($\mu$m) | 30 | 250 | — | 50 |

The dressings were tested in a Frantz cell for 72 hours.

Tests showed that the product I released 52% more triamcinolone acetoid than product II during the 72 hours.

What is claimed is:

1. A dressing for dosing one or more medicaments and comprising at least one medicament containing layer and a barrier layer arranged between the medicament containing layer and as release face, characterized in that the barrier layer is a continuous hydrophobic phase and a discontinuous hydrophilic phase which is dispersed therein and which is water soluble or water swellable.

2. A dressing according to claim 1, characterized in that it additionally comprises a water-tight top layer (3) and either the hydrophobic phase of the barrier layer contains an adhesive or an adhesive layer is an additional layer (4) arranged on the face of the barrier layer intended to face a wound or skin face.

3. A dressing according to claim 1, characterized in that the discontinuous phase is at least one water soluble or water swellable hydrocolloids, starch or cellulose derivatives or hydrophilic polymers.

4. A dressing according to claim 1, characterized in that at least one medicament, is incorporated in at least one of the discontinuous or continuous phases of the barrier layer.

5. A dressing according to claim 1, characterized in that the barrier layer is composed of
   (I) a continuous phase containing
      (a) a physically cross-linked elastomer comprising polyisobutylene, styrene olefin styrene block copolymer or ethylene propylene block copolymer, and optionally one or more of the components stated in items b–e,
      (b) a hydrocarbon resin in the form of a polymer or copolymer of cyclopentadiene, dicyclopentadiene, $\alpha$-pinene, $\beta$-pinene or mixture thereof,
      (c) an antioxidant,
      (d) a mineral oil extender, and
      (e) an elastomer polar plasticizer,
   (II) a phase dispersed in the continuous phase comprising water swellable hydrocolloid.

6. A dressing according to claim 1, characterized in that the medicament layer comprises a hydrophobic polymer matrix.

7. A dressing according to claim 6, characterized in that the medicament layer additionally contains a discontinuous hydrophilic phase.

8. A dressing according to claim 7, characterized in that the medicament or the medicaments are incorporated in the hydrophobic continuous phase.

9. A dressing according to claim 7, characterized in that the medicament or the medicaments are incorporated in the hydrophilic discontinuous phase.

10. A dressing according to claim 7, characterized in that the medicament or the medicaments are incorporated in both the continuous phase and the discontinuous phase.

11. A dressing according to claim 1, characterized in that it comprises at least two medicament layers having a different medicament content or the same medicament content.

12. A dressing according to claim 11, characterized in that it comprises at least two barrier layers.

13. A dressing according to claim 2, characterized in that it comprises a liquid absorbing medicament-free layer arranged between the top and the medicament layer or the upper medicament layer if several such layers are provided.

14. A dressing according to claim 2, characterized in that the water-tight top layer is water vapor permeable, the hydrophobic phase of the adhesive-containing barrier layer comprises an elastomer, a plasticizer and a tackifying resin and the additional adhesive layer is patterned.

15. A dressing according to claim 3, characterized in that the hydrophilic polymer is at least one water soluble or water swellable hydrocolloid.

16. A dressing according to claim 3, characterized in that the hydrocolloid is sodium carboxymethylcellulose.

17. A dressing according to claim 4, characterized in that the amount of medicament in the barrier layer is less than the medicament in the medicament containing layer.

18. A dressing according to claim 5, characterized in that the plasticizer is an ester of a polyethylene or polypropylene glycol or of a di- or polybasic carboxylic acid with an aliphatic alcohol, and wherein the barrier layer has a filling degree of 20–60% by volume.

19. A dressing according to claim 6, characterized in that the hydrophobic polymer matrix comprises an elastomer, plasticizer, tackifying resin and optionally an oil-based extender and antioxidant.

20. A dressing according to claim 7, characterized in that the discontinuous hydrophilic phase comprises at least one water soluble or water-swellable hydrocolloid and the filling degree is less than 50% by volume.

21. A dressing according to claim 13, characterized in that the liquid absorbing medicament-free layer has the same structure as the medicament containing layer and a filling degree of more than 40% by volume.

* * * * *